(12) United States Patent
Juels et al.

(10) Patent No.: US 8,515,070 B2
(45) Date of Patent: Aug. 20, 2013

(54) ACCESS CONTROL FOR IMPLANTED MEDICAL DEVICES

(75) Inventors: Ari Juels, Brookline, MA (US); Daniel Vernon Bailey, Pepperell, MA (US)

(73) Assignee: EMC Corporation, Hopkinton, MA (US)

( * ) Notice: Subject to any disclaimer, the term of this patent is extended or adjusted under 35 U.S.C. 154(b) by 1031 days.

(21) Appl. No.: 12/251,036

(22) Filed: Oct. 14, 2008

(65) Prior Publication Data

US 2009/0125084 A1    May 14, 2009

Related U.S. Application Data

(60) Provisional application No. 60/979,580, filed on Oct. 12, 2007.

(51) Int. Cl.
  *H04K 1/00* (2006.01)
  *H04Q 5/22* (2006.01)
  *A61N 1/00* (2006.01)

(52) U.S. Cl.
  USPC .............. 380/270; 607/30; 607/31; 607/32; 607/59; 607/60; 340/10.1; 340/5.82

(58) Field of Classification Search
  USPC .............. 607/30–32, 59, 60; 340/10.1, 5.82; 380/270
  See application file for complete search history.

(56) References Cited

U.S. PATENT DOCUMENTS

| | | | |
|---|---|---|---|
| 6,970,070 B2 | 11/2005 | Juels et al. | |
| 7,298,243 B2 | 11/2007 | Juels et al. | |
| 2004/0015207 A1* | 1/2004 | Barriskill et al. | 607/49 |
| 2004/0222878 A1 | 11/2004 | Juels | |
| 2005/0065445 A1* | 3/2005 | Arzbaecher et al. | 600/515 |
| 2006/0022799 A1 | 2/2006 | Juels | |
| 2006/0033608 A1 | 2/2006 | Juels et al. | |
| 2007/0194889 A1 | 8/2007 | Bailey et al. | |
| 2007/0195960 A1* | 8/2007 | Goldman et al. | 380/286 |

OTHER PUBLICATIONS

Bao, Shu-Di et al, "A Novel Key Distribution of body area networks for telemedicine" 2004, IEEE International Workshop on Biomedical Circuits &Systems, S2 p. 1-18 to 1-19.*

S-D. Bao et al., "Physiological Signal Based Entity Authentication for Body Area Sensor Networks and Mobile Healthcare Systems," IEEE, 27th Annual International Conference of Engineering in Medicine and Biology Society, Sep. 2005, pp. 2455-2458.

(Continued)

*Primary Examiner* — Niketa Patel
*Assistant Examiner* — William Levicky
(74) *Attorney, Agent, or Firm* — Ryan, Mason & Lewis, LLP (57) ABSTRACT

Enhanced security is provided in a system comprising a medical device and a monitoring device. The medical device is configured for implantation into a living organism, and comprises processing circuitry and an interface for communicating with the monitoring device. Access to the medical device by the monitoring device is controlled based on measurement of one or more physiological values of the living organism by at least one of the two devices. In an illustrative embodiment, the medical device and the monitoring device are configured to include respective physiological value sensors for measuring respective dynamic physiological values of the living organism. The medical device is further configured to determine if the dynamic physiological values are sufficiently similar to one another and to grant or deny the monitoring device access to the medical device based on the determination.

25 Claims, 4 Drawing Sheets

(56) References Cited

OTHER PUBLICATIONS

X. Boyen et al., "Secure Remote Authentication Using Biometric Data," EUROCRYPT, LNCS, 2005, vol. 3494, pp. 147-163.

J. Clulow et al., "So Near and Yet So Far: Distance-Bounding Attacks in Wireless Networks," ESAS 2006, LNCS, 2008, vol. 4357, pp. 83-97.

G.I. Davida et al., "On Enabling Secure Applications Through Off-Line Biometric Identification," IEEE Symposium on Privacy and Security, 1998, 11 pages.

Y. Dodis et al., "Robust Fuzzy Extractors and Authenticated Key Agreement from Close Secrets," CRYPTO, LNCS, 2006, vol. 4117, pp. 18 pages.

Y. Dodis et al., "Fuzzy Extractors: How to Generate Strong Keys from Biometrics and Other Noisy Data," EUROCRYPT, LNCS, 2004, vol. 3027, pp. 523-540.

K. Fishkin et al., "Some Methods for Privacy in RFICCommunication," 1st European Workshop on Security in Ad-Hoc and Sensor Networks (ESAS), 2004, pp. 1-13.

J. Halamka, M.D. et al., "The Security Implications of VeriChip Cloning," Journal of the American Medical Informatics Association, Technology Evaluation, Nov./Dec. 2006, pp. 601-607, vol. 13, No. 6.

Integrated Medical Devices, Inc., PSD 410 Pacemaker Produce Overview, http://www.integrated-medical.com/pacemaker.html. 2007, 1 page.

A. Juels et al., "A Fuzzy Vault Scheme," Designs, Codes, and Cryptography, 2006, 18 pages, vol. 38, No. 2.

A. Juels et al., "A Fuzzy Commitment Scheme," ACM Press, Sixth ACM Conference on Computer and Communications Security, 1999, pp. 28-36.

K. Lorincz et al., "Sensor Networks for Emergency Response: Challenges and Opportunities," IEEE, Pervasive Computing, 2004, pp. 16-23, vol. 3, No. 4.

C.C.Y. Poon et al., "A Novel Biometrics Method to Secure Wireless Body Area Sensor Networks for Telemedicine and M-Health," IEEE Communications Magazine, Apr. 2006, pp. 73-81, vol. 44, No. 4.

S. Cherukuri et al., "BioSec: A Biometric Based Approach for Securing Communication in Wireless Networks of Biosensors Implanted in the Human Body," Proceedings of the International Conference on Parallel Processing Workshops, 2003, pp. 432-439.

J. Suomalainen et al., "Security Associations in Personal Networks: A Comparative Analysis," ESAS 2007, LNCS, 2007, pp. 43-57, vol. 4572.

\* cited by examiner

ACCESS CONTROL FOR IMPLANTED MEDICAL DEVICES

RELATED APPLICATION(S)

The present application claims the priority of U.S. Provisional Patent Application Ser. No. 60/979,580, filed Oct. 12, 2007 and entitled "Securing Emergency Access to Implanted Medical Devices," the disclosure of which is incorporated by reference herein.

FIELD OF THE INVENTION

The present invention relates generally to medical devices, and more particularly to medical devices that are implantable in humans or other living organisms and that communicate wirelessly with external monitoring devices.

BACKGROUND OF THE INVENTION

Implanted medical devices (IMDs) that communicate wirelessly with external monitoring and control systems are becoming commonplace in the medical world. Certain pacemakers, for example, are subject to reprogramming by medical personnel over the telephone. One vendor sells human-implantable radio frequency identification (RFID) tags to combat the "John Doe" problem in medical environments, cases in which disoriented or unconscious patients lack adequate identity documents. Similar implanted devices are already in widespread use for identification of lost house pets. More broadly, a new medical frontier is developing around both implantable sensors that relay physiological values by radio to monitoring devices and medical control devices subject to external reprogramming. These and other types of IMDs offer the prospect of continuous, automated production of diagnostic data and physiological intervention.

Of course, IMDs are computing devices of the utmost security sensitivity. A sensor or identification tag can expose privacy-sensitive data to compromise. A malefactor capable of reprogramming an implanted medical control device can injure or kill a victim.

At the same time, IMDs must allow rapid, unimpeded access by medical personnel. A patient's life may depend on the ability of first responders to gain swift access to his or her IMDs. An access-control system that requires emergency medical technicians to reference a secure database, obtain a password from the patient, or access a patient's wallet or handbag poses a threat to timely medical intervention.

A conventional approach to providing secure access to IMDs is described in S. K. S. Gupta et al. "BioSec: A biometric based approach for securing communication in wireless networks of biosensors implanted in the human body," ICPP Workshops: International Workshop on Wireless Security and Privacy," pp. 432-439, 2003. This architecture assumes communication between IMDs and a base station. The base station acts as a point of aggregation of IMDs and as a point of contact for external medical systems. The base station makes use of a pre-established, long-term shared symmetric key to communicate with each IMD. The IMDs communicate with one another using a freshly derived key based on a current physiological value.

Other security architectures for IMDs rely on standard cryptographic access-control approaches involving the pre-provisioning of keys in IMDs and their associated monitoring devices. See, for example, K. Lorincz et al., "Sensor networks for emergency response: Challenges and opportunities," Pervasive Computing, 3(4):1623, 2004.

Unfortunately, these and other conventional techniques fail to provide an adequate solution to the problem of emergency access to IMDs.

It is apparent from the foregoing that a strong tension exists between the requirements of IMD security and IMD accessibility. What is needed is an approach that achieves a suitable balance between these competing requirements.

SUMMARY OF THE INVENTION

The present invention in illustrative embodiments provides techniques for secure access to IMDs from a monitoring device.

In an aspect of the invention, a medical device is configured for implantation into a living organism, and comprises processing circuitry and an interface for communicating with the monitoring device. Access to the medical device by the monitoring device is controlled based on measurement of one or more physiological values of the living organism by at least one of the two devices.

In one of the illustrative embodiments, both the medical device and the monitoring device are configured to include physiological value sensors for measuring respective dynamic physiological values V1 and V2 of the living organism. The medical device determines if the dynamic physiological values V1 and V2 are sufficiently close. For example, the medical device may determine if the magnitude of the difference between the two values is less than or equal to a specified threshold, with the monitoring device being granted access to the medical device only if the magnitude of the difference between the two values is less than or equal to the specified threshold.

In other embodiments, physiological values are measured by only the medical device or only the monitoring device, rather than by both devices as in the above-described illustrative embodiment.

Advantageously, the present invention in the illustrative embodiments disclosed herein provides simple and efficient techniques for providing enhanced security in IMD devices, in a manner that achieves a suitable balance between the competing requirements of security and accessibility.

These and other features and advantages of the present invention will become more readily apparent from the accompanying drawings and the following detailed description.

DETAILED DESCRIPTION

The present invention will be described herein with reference to an exemplary IMD system in which multiple IMDs communicate with a medical monitor. It is to be appreciated, however, that the invention is not restricted to use in this or any other particular IMD system configuration.

The term "IMD" as used herein is intended to include, for example, an RFID tag or any other type of implantable medical device configurable for wireless communication with one or more external monitors.

The terms "monitor" or "monitoring device" as used herein are intended to include, for example, an RFID tag reader or any other type of device capable of interacting with an IMD so as to receive medical information or other information from the IMD. Monitoring devices may therefore include, again by way of example, devices that receive physiological values by radio from IMDs, as well as devices that are able to reprogram or otherwise control IMDs.

Figure 1:
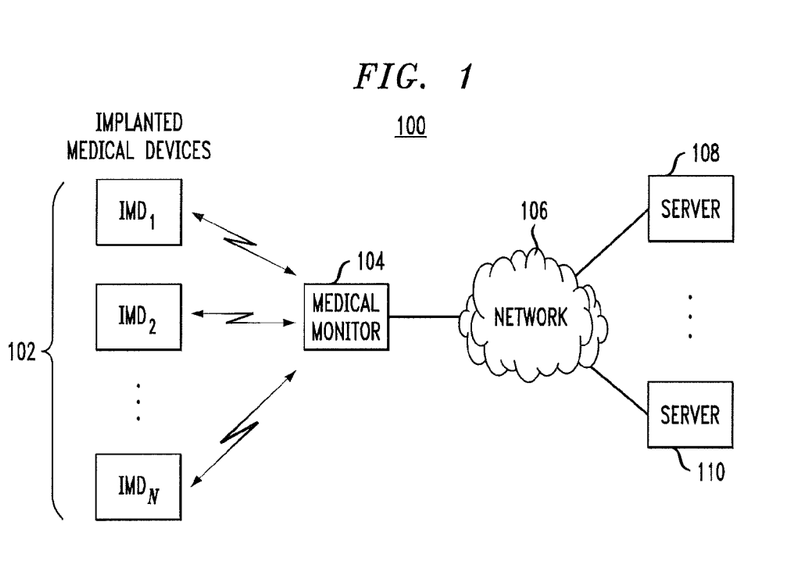
FIG. 1 is a simplified block diagram of an exemplary IMD system in which the present invention is implemented in one embodiment.

FIG. 1 shows an IMD system 100 in which the present invention is implemented. The system 100 includes a number N of IMDs 102, more particularly denoted by their associated identifiers $IMD_1, IMD_2, \ldots IMD_N$, and a medical monitor 104. The monitor 104 communicates with the IMDs 102 and receives medical information therefrom. Such information may include, for example, one or more transmitted identifiers, diagnostic data, measured physiological values, etc. The monitor 104 is coupled via a network 106 to servers denoted 108, 110. Although not explicitly shown in FIG. 1, a verifier may be associated with the monitor 104. Such a verifier may be implemented, for example, using one or both of the servers 108, 110, another network element accessible via the network 106, or another system element coupled to or otherwise associated with the monitor 104.

The IMDs 102 are each configured for implantation into a living organism, such as a human being. The IMDs may each be implanted in a separate living organism, or multiple such IMDs may be implanted in each of one or more living organisms. Such organisms are omitted from the figure for simplicity and clarity of illustration. The medical monitor 104 is typically arranged external to the living organism(s).

A given IMD 102 in accordance with the invention generally includes circuitry comprising memory, processing logic and an RF transceiver. These elements may be configured in a manner similar to that used in conventional IMDs.

As indicated above, one or more of the IMDs 102 may comprise respective RFID tags. A conventional RFID tag typically comprises an integrated circuit transceiver capable of transmitting information to a nearby reader in response to a query from the reader. Many RFID tags are "passive" in that they do not include a battery or other power source, but instead obtain the power necessary to operate from the query signal itself.

Additional details regarding illustrative RFID systems that may be utilized in implementing aspects of the present invention can be found in, for example, U.S. Pat. No. 6,970,070 entitled "Method and Apparatus for Selective Blocking of Radio Frequency Identification Devices," U.S. patent application Ser. No. 10/782,309, filed Feb. 19, 2004 and entitled "Low-Complexity Cryptographic Techniques for use with Radio Frequency Identification Devices," U.S. Pat. No. 7,298,243 entitled "Radio Frequency Identification System with Privacy Policy Implementation based on Device Classification," U.S. patent application Ser. No. 11/191,633, filed Jul. 28, 2005 and entitled "Methods and Apparatus for RFID Device Authentication," U.S. patent application Ser. No. 11/193,729, filed Jul. 29, 2005 and entitled "Proxy Device for Enhanced Privacy in an RFID System," and U.S. patent application Ser. No. 11/671,275, filed Feb. 5, 2007 and entitled "Security Provision in Standards-Compliant RFID Systems," all of which are commonly assigned herewith and incorporated by reference herein.

It is to be appreciated, however, that the IMDs 102 need not be implemented as RFID tags. Any of a wide variety of medical devices capable of communicating with external monitoring devices may be used.

The network 106 may represent a global computer network such as the Internet, a wide area network (WAN), a local area network (LAN), a satellite network, a telephone or cable network, or various portions or combinations of these and other types of networks. The servers 108, 110 may be conventional processor-based information processing devices of a type conventionally utilized in conjunction with IMD monitors in an IMD system.

The particular number N of IMDs 102 in the system 100 is purely arbitrary, and the system can be configured to support any desired number of such devices. Also, although only a single monitor 104 is shown in the figure for simplicity and clarity of illustration, the system may include multiple monitors. Furthermore, it should be noted that a given monitor need not be connected to a network, and may instead operate as a stand-alone device, or may be only intermittently connected to the network. Also, a given monitor can be directly connected to a server or other system element, rather than connected thereto over a network as illustrated in the example system 100.

Figure 2:
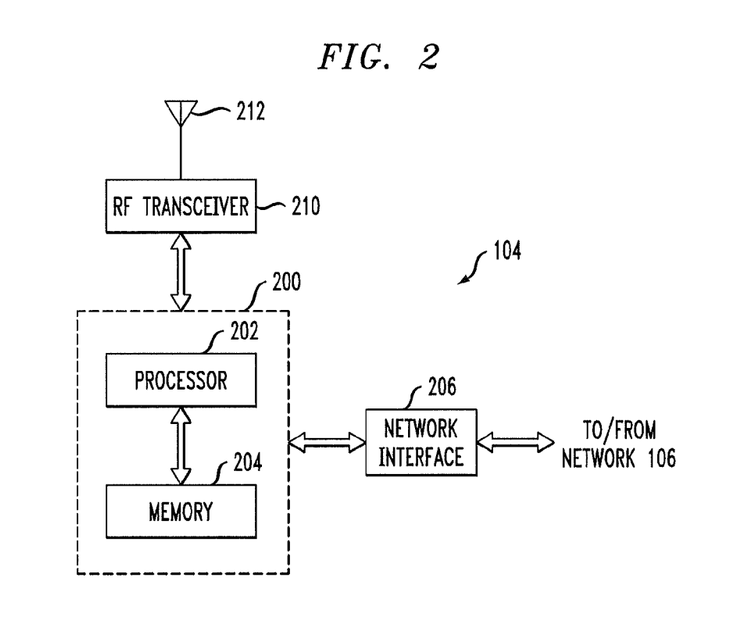
FIG. 2 illustrates one possible implementation of a medical monitor of the FIG. 1 system.

FIG. 2 shows one possible implementation of the medical monitor 104 of the FIG. 1 system. Such a medical monitor is an example of what is more generally referred to herein as a "monitoring device." The medical monitor in this implementation includes a processing block 200, comprising a processor 202 coupled to a memory 204, a network interface 206, an RF transceiver 210, and an antenna 212. One or more of these elements may be implemented in whole or in part as a conventional microprocessor, digital signal processor, application-specific integrated circuit (ASIC) or other type of circuitry, as well as portions or combinations of such circuitry elements. Software programs for controlling the operation of the monitor 104 may be stored in the memory 204 and executed by the processor 202. The memory 204, and other memories referred to herein, may comprise, for example, random access memory (RAM), read-only memory (ROM), electrically erasable programmable ROM (EEPROM), or other types of storage elements, in any combination.

The medical monitor 104 may be implemented in or otherwise comprise at least a portion of a mobile telephone, a portable computer, a personal digital assistant (PDA), a hardware-based authentication token such as an RSA SecurID® token, or any other type of processing device utilizable in communicating with an IMD as described herein. The invention thus does not require any particular monitoring device configuration.

Figure 3:
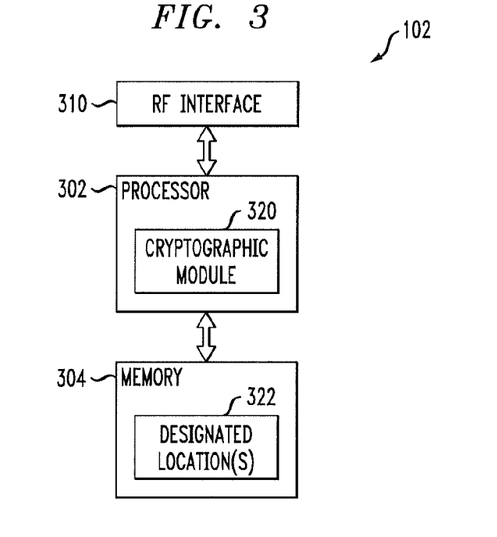
FIG. 3 illustrates one possible implementation of a given IMD of the FIG. 1 system.

FIG. 3 shows one possible implementation of a given one of the IMDs 102 of the FIG. 1 system. The IMD comprises a processor 302 coupled to a memory 304, and an RF interface 310 which may comprise, for example, an RF transceiver and an associated antenna. The processor may be in the form of relatively simple processing logic, or may represent a more complex processor. In the implementation shown, the processor 302 implements a cryptographic module 320, which may comprise, for example, an encryption engine, a fuzzy extractor, or other processing element(s) providing cryptographic functionality as described herein. The cryptographic module may comprise one or more software programs that are stored in memory 304 and executed by processor 302.

The memory 304 comprises one or more designated locations 322, which may be accessible to both the IMD 102 and to the monitor 104. The monitor may be required to submit a personal identification number (PIN) or other authentication information in order to access the designated locations 322. The designated locations 322 may comprise substantially the entire memory of the IMD 102, or just a designated subset of the IMD memory. For example, the memory 304 may be organized in the form of multiple banks, with one or more of the banks being designated as accessible to the monitor 104.

The memories 204 and 304 are examples of what are more generally referred to herein as processor-readable storage media. Other examples of such media that may be used to store software programs for use in implementing the present invention include computer disks, storage drives, etc.

The present invention in the illustrative embodiments provides controlled access to one or more of the IMDs 102 by the medical monitor 104 based on measurement of physiological values (PVs) of the associated living organism(s). This access control may rely, for example, upon physical contact with or proximity to a patient or other living organism in which an IMD has been implanted. The physiologic values change over time and thus serve as a dynamic biometric for access control. This arrangement ensures "freshness" of the biometric in typical emergency access scenarios in which a given IMD 102 may have no preexisting relationship with the medical monitor 104. Dynamic physiological values are thus distinct from static physiological values such as fingerprints and retina scans that generally do not change significantly over time.

There are many PVs that are time-varying and thus suitable for use as a dynamic biometric in a given embodiment of the invention. These include, by way of example, inter-pulse interval (IPI), heart rate variance (HRV), electrocardiogram measurements (EKG), photoplethysmograms (PPG), brainwaves, etc.

A given IMD 102 may also be configured to provide a failsafe mode of operation in which it openly broadcasts an access control key if it detects the absence of one or more essential PVs, even if those PVs are used to support IMD access control under normal circumstances. For example, a patient may have an IMD that utilizes PVs based on bloodflow as a dynamic biometric. In an emergency access scenario, that patient's heart may have stopped, such that PVs based on bloodflow are no longer available. The failsafe mode of operation allows emergency personnel to obtain the needed information in such a situation. The failsafe mode of operation is also referred to herein as "flatline" access control.

It should be noted that an IMD system in accordance with the invention can supplement its dynamic biometrics based on PVs with conventional static biometrics such as fingerprints or retina scans.

For purposes of further describing certain illustrative embodiments, the IMDs 102 may be classified into two general types, namely, sensor IMDs and actuator IMDs. Sensor IMDs emit data but do not accept control information. Sensor IMDs may include output-only sensor IMDs, as well as sensor IMDs that are capable of supporting interactive protocols. Actuator IMDs, by contrast, are subject to configuration through radio contact with medical systems. Different access control techniques will be described below for each of these two general classes of IMDs. It is to be appreciated, however, that the techniques of the present invention can be implemented using other types of IMDs.

The problem of securing medical monitor access to an IMD is essentially a problem of device pairing, an extensively investigated topic in data security. A substantial literature has addressed the problem of how to establish a cryptographic key between two wireless devices given a short, shared PIN and the intermediation of a human user, causing these protocols to sometimes be called user-verified key establishment. See J. Suomalainen et al., "Security associations in personal networks: A comparative analysis," Security and Privacy in Ad-Hoc and Sensor Networks, pp. 43-57, Springer-Verlag, 2007, LNCS vol. 4572. Also, a new generation of strong pairing protocols for Bluetooth, wireless USB, and Wi-Fi is currently undergoing standardization.

For simplicity in the following description, the medical monitor 104 of FIG. 1 may at times be referred to as an MM.

The challenge of pairing IMDs and MMs differs from that of standard wireless devices in several respects. First, the major challenge is that of deriving a shared PIN or other shared secret. In most wireless pairing protocols, the user is presumed to key a PIN into his or her devices or to perform a visual comparison between displayed PINs. Additionally, the noisy, dynamic nature of IMD-MM pairing is unusual, and output-only sensor IMDs in fact have no clear-cut parallel among common wireless consumer appliances.

As a sensor IMD serves exclusively to emit diagnostic information, it can be implemented as an output-only device as previously indicated. Indeed, conservative security engineering argues in favor of restricting data inputs to IMDs, in that input channels increase the vulnerability of a device to active attack.

Illustrative embodiments of access control protocols that may be carried out between a given IMD 102 and the medical monitor 104 will now be described with reference to FIGS. 4 and 5.

Figure 4:
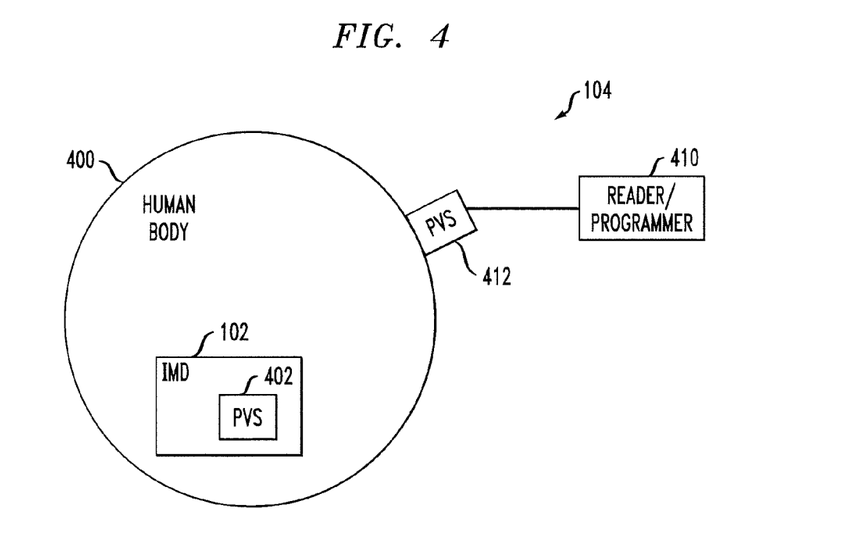
FIG. 4 shows a more detailed view of one possible implementation of a portion of the IMD system of FIG. 1 in which both an IMD and a medical monitor include respective physiological value sensors.

Referring now to FIG. 4, it can be seen that a given IMD 102 is implanted into human body 400. The IMD 102 comprises a PV sensor (PVS) 402. The medical monitor 104 in this embodiment comprises a reader/programmer 410 and a PVS 412. The reader/programmer, which may comprise a reader, a programmer or both, is coupled to the PVS 412. The IMD 402 and the medical monitor 104 use their respective PVS elements 402, 412 to measure PVs of the human body 400.

Thus, in the FIG. 4 embodiment, both the IMD 102 and the medical monitor 104 measure PVs of the human body 400. In other embodiments, PVs may be measured by only one of these two devices, either by the IMD alone or the medical monitor alone.

A general access control protocol suitable for use with the arrangement illustrated in FIG. 4 will now be described in conjunction with the flow diagram of FIG. 5. In steps 500 and 502, the IMD 102 and the medical monitor 104 sense respective PVs V1 and V2 utilizing their respective PVS elements 402, 412. Also, in step 504, a wireless communication session is established between the IMD and the medical monitor. The particular ordering of steps 500, 502 and 504 shown in FIG. 5 is arbitrary. These steps could occur in any order.

In step 506, the IMD 102 determines whether the V1 value measured by its PVS element 402 is sufficiently close to the V2 value measured by the PVS element 412 of the medical monitor 104. This determination may involve, for example, determining if the magnitude of the difference between V1 and V2 is less than or equal to a designated threshold. In other embodiments, the determination of closeness may be based on other functions of V1 and V2.

If the determination in step 506 indicates that V1 and V2 are sufficiently close, the IMD grants access to the medical monitor in step 508. That is, the IMD allows the medical monitor to obtain medical information or other information from the IMD. However, if the determination in step 506 indicates that V1 and V2 are not sufficiently close, the IMD denies access to the medical monitor as indicated in step 510.

Figure 5:
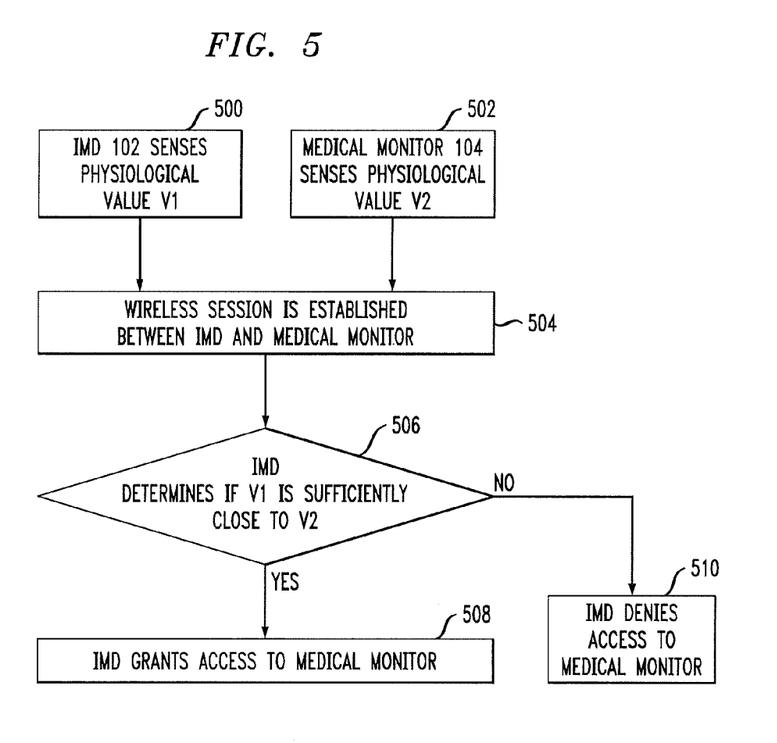
FIG. 5 is a flow diagram showing portions of an access control protocol carried out between the IMD and medical monitor of FIG. 4.

The access control protocol of FIG. 5 is an example of an arrangement in which the IMD 102 is granting access based on the ability of the medical monitor 104 to measure a dynamic PV that is similar to one measured by the IMD itself. Other embodiments may involve both the IMD and the medical monitor reading and comparing the same or related PVs.

In an alternative access control protocol, the medical monitor 104 transmits an encrypted and possibly integrity protected PV and session key to the IMD 102. These values can be encrypted under a symmetric or public key emitted by the IMD. The IMD may also be configured to emit a certificate containing the name of the patient in order to allow the medical monitor to determine that the key belongs to the IMD of interest. The IMD then checks the validity of the PV.

It should be noted that the term "access" as used herein is intended to be construed broadly. Thus, for example, an IMD may grant access by releasing information to the medical monitor that would not otherwise be released. As another example, the IMD may grant access to the medical monitor by allowing the monitor to read information from the designated location(s) 322 in memory 304. Numerous other types of access may be supported using the access control techniques disclosed herein.

The determination made in step 506 of the FIG. 5 access control protocol may be based on the use of fuzzy extraction, as will now be described in greater detail.

Let $$Gen(w) \xrightarrow{R} (P, R)$$

denote a fuzzy extractor which, given a fuzzy input value w, outputs a key R and public value P. A corresponding algorithm $Rec(w',P) \rightarrow R$ outputs the key R given $w' \approx w$, i.e., a value w' that is sufficiently close to the value w in a suitable metric, such as the magnitude of the difference between the values. The algorithm Rec is considered to be robust if it is secure against modification of P, i.e., detects message modification. Additional details on fuzzy extractors can be found in, for example, Y. Dodis et al., "Robust fuzzy extractors and authenticated key agreement from close secrets," CRYPTO 2006, pp. 232-250, Springer-Verlag, 2006, LNCS vol. 4117; and Y. Dodis et al., "Fuzzy extractors: How to generate strong keys from biometrics and other noisy data," Eurocrypt 2004, pp. 523-540, Springer-Verlag, 2004, LNCS vol. 3027.

An access control protocol for sensor IMDs involving outputs that are encrypted and authenticated under PV data is as follows. This protocol utilizes the above-described fuzzy extractor. In particular, the sensor IMD computes $Gen(PV_t)$ $\rightarrow (R_t, P_t)$ and outputs $(P_t, Enc_{R_t}[\delta_t])$, where t denotes the current time interval, $PV_t$ is the measured physiological value at time t, and $\delta_t$ is medical information or other information of the IMD. Given $PV'_t \approx PV_t$, an MM can then compute $\delta_t$. Given a robust extractor, the MM can additionally achieve assurance of the integrity of the IMD information, i.e., that $\delta_t$ was encrypted by the target IMD or at least by a device with approximate knowledge of $PV_t$.

It should be noted that the value $PV_t$ need not involve measurement of a PV exclusively during a current time interval t, but may derive from measurements over a set or sequence of time intervals.

The public value $P_t$ may leak some information about the $PV_t$, potentially to the detriment of the privacy of the IMD bearer. An alternative approach is for the MM to initiate communication with the IMD, that is, to compute $Gen(PV_t)$ $\rightarrow (R_t, P_t)$ and transmit $P_t$ to the IMD. The IMD, on computing $R_t$, and verifying the correctness of $P_t$ if Gen is a robust extractor, would output $Enc_{R_t}[\delta_t]$. The MM then computes $\delta_t$ from the encryption $Enc_{R_t}[\delta_t]$ using the key $R_t$.

Figure 6:
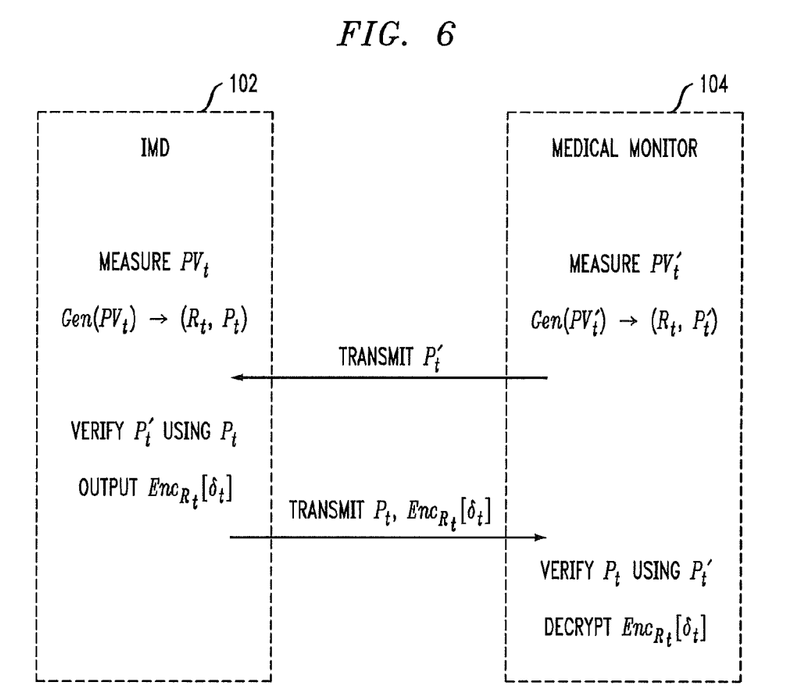
FIG. 6 illustrates at least a portion of an access control protocol carried out between the IMD and medical monitor of FIG. 4.

At least a portion of an illustrative embodiment of an access control protocol in accordance with this approach is illustrated in FIG. 6. It is to be appreciated, however, that embodiments are not limited solely to the access control protocol illustrated in FIG. 6.

This latter approach is suitable as well for establishing a session between an MM and an actuator IMD. The key $R_t$ can serve as a shared key for the two devices. In this case, a robust fuzzy extractor is essential, as the actuator IMD must be able to authenticate the MM. Authentication of the IMD to the MM is also important, but is implicit in the ability of the IMD to compute $R_t$. The key $R_t$ or any derivative keys can be used for both standard encryption and authentication.

Other embodiments may utilize hybrid approaches in which, for example, PVs are used to update long-term keys or keys are derived from PVs that are measured over a long period of time.

Low-entropy protocols may also be used. Deriving high-entropy secrets from biometric data has proven challenging in practice, as attested by, e.g., the false acceptance rates (FARs) of fingerprint readers. Typical commercial fingerprint readers claim FARs in the vicinity of 1:100,000 or 1:1,000,000, implying fewer than 20 bits of extractable entropy from a finger. In the case of secret keys derived from PVs, the shorter the key, the more rapid the harvesting. Hence, it may be desirable to implement an IMD access control protocol that relies on a low-entropy secret shared by an IMD and MM.

For an output-only sensor IMD, one possible approach relies on non-redundant encryption. Suppose that $\delta_t \in \Delta$, i.e., A is the message space for the emission of the sensor IMD. The sensor IMD outputs $(P_t, C_t = \tilde{E}nc_{R_t}[\delta_t])$, where $\tilde{E}nc$ is a non-redundant encryption for $\Delta$, i.e., one such that a corresponding decryption $\tilde{D}ec_k[C_t] \in \Delta$ for any valid decryption key k. An adversary is then unable to recover $\delta_t$ via brute-force key search.

For a sensor IMD that supports interactive protocols, one possible approach is to split $PV_t$ into two independent values, $PV1_t$ and $PV2_t$. The MM can authenticate to the sensor IMD using $PV1_t$ emitting $PV1_t$ in the clear. This results in some privacy compromise, but only in the rare event of MM access to the IMD. The sensor IMD can then emit a ciphertext on $\delta_t$ using non-redundant encryption under a key derived from $PV2_t$.

Alternatively, it is possible to use a fuzzy extractor to convert a short, noisy secret, into the equivalent of a password that may then play a role in a standard password-based key-agreement protocol. Such an embodiment may utilize techniques similar to those described in Boyen et al., "Secure remote authentication using biometric data," EUROCRYPT 2005, pp. 147-163, Springer-Verlag, LNCS vol. 3494.

A drawback to this approach is its reliance on public-key cryptography, and the consequent resource requirements for the IMD. Additionally, the Boyen et al. approach leaks data in the form of $P_t$. An alternative public-key based key-agreement protocol may not engender such data leakage.

A significant threat to IMD access control systems based on short secrets is denial-of-service. Such systems must apply a form of throttling to access attempts in order to prevent brute-force attacks. That same throttling mechanism can be exploited by an attacker to disable an IMD for a period of time. Thus, the IMD should implement an appropriate throttling mechanism. One possible option is to use an arrangement analogous to the "next passcode" mode implemented for RSA SecurID® tokens. When a number of authentication failures take place, the SecurID® system requires the user to enter not one valid passcode, but two in succession. Similarly, given a number of authentication failures, an IMD can require additional PV measurements for access. This approach has the advantage of requiring only a relatively short measurement in a benign environment, but permitting access at the cost of greater access time in a hostile environment.

A number of alternative or supplementary authentication techniques may be used in illustrative embodiments of the invention, as will now be described. These techniques include distance bounding, distinguished gestures, and directionality measurements, and can be used individually or in any combination.

An IMD 102 can be configured to utilize distance bounding techniques to provide enhanced access control. For example, the IMD can be configured to determine its approximate distance from the medical monitor 104 and prevent medium-to-long-range access. Access is granted only if the medical monitor is determined to be in sufficiently close physical proximity to the IMD. See, for example, J. Clulow et al., "So near and yet so far: Distance-bounding attacks in wireless networks," Security and Privacy in Ad-Hoc and Sensor Networks, pp. 83-97, Springer-Verlag, 2006, LNCS vol. 4357. The IMD can determine its distance from the medical monitor by, for example, measuring the signal-to-noise ratio of communications received from the medical monitor. See, for example, K. P. Fishkin et al., "Some methods for privacy in RFID communication," 1st European Workshop on Security in Ad-Hoc and Sensor Networks (ESAS 2004), 2004.

Distinguished gestures or other types of movements may also or alternatively be used to provide access control in a given embodiment of the invention. For example, predetermined types of special or unusual positioning or other movement of a patient might be used to trigger release of a current access key for an IMD of that patient. As a more particular example, a collection of IMDs might be configured to detect a patient placing each of his or her forefingers on a particular rib.

Other embodiments may utilize directionality of received signals to provide access control. For example, an IMD can be configured with antennas that allow it to determine the directionality of a given received signal. As a more particular example, an IMD can be configured to determine whether a signal originates from a source on the left or the right side of the IMD. A medical monitor could be configured with transmitters arranged on two sides of the patient, and to emit an authenticable sequence of values (e.g., pre-images in a hash chain) in rapid lateral alternation, such that the IMD can achieve assurance that the monitor is properly configured. It is possible that an attacker could position transmitters on either side of the patient (e.g., in a doorway) in order to defeat such a system.

Communications between the IMDs 102 and the medical monitor 104 in system 100 utilize RF channels, but this is by way of illustrative example only. A wide variety of alternative channels may be used, including, for example, infrared channels, acoustic channels, or channels involving other types of signals known to penetrate living tissue.

As a more particular example, a given IMD could be configured to include an infrared detector to provide a data input path from the medical monitor. Data could be modulated using light pulse rate, wavelength, polarity, or pulse duration. An IMD of this type could be used in conjunction with a medical monitor comprising or coupled to a low-level light therapy (LLLT) device. Because of the combination of short range and line-of-sight, an LLLT would provide evidence of the locality of an MM to an IMD, and could serve as a unidirectional or even bidirectional data path between an MM and an IMD. The relative resistance of LLLT to eavesdropping would permit an MM to pass a secret cryptographic key to the IMD or vice versa. This key could serve to encrypt IMD data transmitted over a potentially less secure medium like RF or to secure a session between an IMD and MM.

Another example of a possible alternate data channel is one based on transcutaneous electrical nerve stimulation (TENS). This involves the application of electrodes directly to the skin. These electrodes supply small amounts of current. Although TENS is contraindicated for pacemaker patients, its electrical signals could be modulated as a data path. It may be possible to reduce the signal amplitude in a TENS device to a point where the signals do not jeopardize the functioning of pacemakers.

Yet another example of a possible alternate data channel is one based on physical contact. For example, Ident Technologies offers a system known as Skinplex that uses human skin as a data transmission medium. Such technologies might offer a different and perhaps complementary platform for proximity-based access-control policies similar in flavor to those enforced by measurement of PVs. It should first be confirmed that any unorthodox communication media of this kind are sufficiently safe and reliable for emergency access control.

Embodiments of the invention may be configured for pre-provisioning of keys. In an embodiment of this type, an MM might carry a digital certificate within a public-key infrastructure (PKI). Given a set of root keys, an IMD could then validate an MM; given an internal clock, the IMD could check the freshness of the MM's credential. PKIs, though, are difficult to implement in practice due to organizational and logistical challenges. Alternatively, MMs might carry a small set of global, symmetric keys provisioned in IMDs. This approach carries a strong risk of key exposure, in that compromise of a single IMD would expose keying material across the entire system. As a supplementary layer of security, however, such an approach is attractive for its simplicity.

It is to be appreciated that the particular configuration, elements and operating parameters of the illustrative embodiments are not requirements of the invention, and should not be construed as limiting the scope of the invention in any way.

For example, the system elements and their configuration as shown in FIGS. 1 through 4 may be varied in alternative embodiments. Similarly, the particular access control protocol steps in the flow diagram of FIG. 5 can be varied in alternative embodiments.

As another example, the techniques of the invention can be applied to medical devices that may not be implanted but are still of a critical nature. In such an embodiment, a medical device may be configured to utilize a high-impedance sensor. High-impedance sensors permit the measurement of certain PVs, e.g., inter-pulse intervals, at a short distance from a patient. They may alleviate the need for a medical device to establish direct contact with a patient but also could represent a threat if they allow too large a read distance.

These and numerous other alternative embodiments within the scope of the appended claims will be readily apparent to those skilled in the art.

What is claimed is:

1. An apparatus comprising:
   a medical device configured for implantation into a living organism, the medical device comprising processing circuitry and an interface configured for communication with an external monitoring device;

wherein the medical device is configured to control access to the medical device by the monitoring device based on a measurement of one or more physiological values of the living organism by the medical device;

wherein access comprises an authorization to modify at least one function of the medical device; and wherein the medical device is further configured to receive a first public value from the monitoring device, to generate a second public value and a key from a given physiological value measured by the medical device, to verify the received first public value using the generated second public value, to encrypt information of the medical device using the key responsive to the verification, and to send the second public value and the encrypted information to the monitoring device.

2. The apparatus of claim 1 wherein the medical device is configured to include a physiological value sensor for measuring a dynamic physiological value V1 of the living organism, the dynamic physiological value V1 being the given physiological value measured by the medical device.

3. The apparatus of claim 2 wherein the medical device is configured to grant or deny the monitoring device access to the medical device based on the monitoring device's ability to decrypt the encrypted information, wherein the key is required to decrypt the encrypted information such that the monitoring device must generate the key from a dynamic physiological value V2 which is sufficiently similar to the dynamic physiological value V1.

4. The apparatus of claim 3 wherein the medical device is configured to generate the key and the second public value using an extractor, such that the key generated from the dynamic physiological value V1 is the same as a key generated from the dynamic physiological value V2 if the magnitude of the difference between the dynamic physiological values V1 and V2 is less than or equal to a specified threshold.

5. The apparatus of claim 1 wherein the medical device computes $Gen(PV_t) \rightarrow (R_t, P_t)$ and outputs $(P_t, Enc_{R_t}[\delta_t])$ to the monitoring device, where t denotes a current time interval, $PV_t$ is the given physiological value measured by the medical device associated with a designated time t, $R_t$ is the key, $P_t$ is the second public value, $\delta_t$ is the information of the medical device, $Gen(PV_t) \rightarrow (R_t, P_t)$ is an extractor that generates from $PV_t$ the key $R_t$ and the second public value $P_t$, and $Enc_{R_t}[\delta_t]$ is an encryption of $\delta_t$ using the key $R_t$.

6. The apparatus of claim 5 wherein $\delta_t$ is encrypted such that it may be decrypted using the first public value and the encryption $Enc_{R_t}[\delta_t]$.

7. The apparatus of claim 5 wherein the extractor is a fuzzy extractor.

8. The apparatus of claim 5 wherein $\delta_t \in \Delta$, where $\Delta$ is a designated message space for the medical device, and the medical device is configured to transmit $(P_t, C_t = \tilde{E}nc_{R_t}[\delta_t])$ to the monitoring device, where $\tilde{E}nc$ is a non-redundant encryption for $\Delta$ such that a corresponding decryption $\tilde{D}ec_k[C_t] \in \Delta$ for any valid decryption key k and $C_t$ is an output of the medical device.

9. The apparatus of claim 1 wherein the given physiological value $PV_t$ is divided into two independent values, $PV1_t$ and $PV2_t$, the first public value being generated using $PV1_t$ and the encrypted information of the medical device being a non-redundant encryption of the information of the medical device using a key derived from $PV2_t$ generated by the medical device.

10. The apparatus of claim 1 wherein the given physiological value is determined from a measurement made by the medical device during a single current time interval.

11. The apparatus of claim 1 wherein the given physiological value is determined from measurements made by the medical device over multiple time intervals.

12. The apparatus of claim 1 wherein the medical device is configured to determine its approximate distance from the monitoring device and to allow access to the medical device by the monitoring device only if the monitoring device is determined to be in sufficiently close physical proximity to the medical device.

13. The apparatus of claim 1 wherein the medical device is configured to detect a predetermined movement of the corresponding living organism and to allow access to the medical device by the monitoring device based at least in part on the detected predetermined movement.

14. The apparatus of claim 1 wherein the medical device is configured to determine directionality of a signal received from the monitoring device and to allow access to the medical device by the monitoring device based at least in part on the determined directionality of the received signal.

15. The apparatus of claim 1 wherein the medical device is configured to modify the given physiological value.

16. The apparatus of claim 1 wherein the medical device is configured to control access to the medical device by the monitoring device utilizing a cryptographic key-agreement protocol which requires the monitoring device to generate the key from a dynamic physiological value that matches or approximates the key generated from a dynamic physiological value measured by the medical device.

17. The apparatus of claim 1, wherein the medical device does not contain pre-existing cryptographic keying material appropriate for mutual authentication of the medical device and the monitoring device.

18. An apparatus comprising:
a monitoring device configured to communicate with one or more medical devices, the monitoring device comprising a processor, a memory coupled to the processor, and interface circuitry coupled to the processor;

wherein the monitoring device is configured to obtain access to a given one of said one or more medical devices based on a measurement of one or more physiological values by the monitoring device;

wherein access comprises an authorization to modify at least one function of the medical device;

wherein the monitoring device is further configured to generate a first public value and a key from a given physiological value measured by the monitoring device, to send the first public value to the medical device, to receive a second public value and encrypted information from the medical device, to verify the received second public value using the generated first public value, and to decrypt the encrypted information using the key responsive to the verification.

19. The apparatus of claim 18 wherein the monitoring device computes $Gen(PV_t) \rightarrow (R_t, P_t)$ and outputs $P_t$ to the medical device, where t denotes a current time interval, $PV_t$ is the given physiological value measured by the monitoring device associated with a designated time t, $R_t$ is the key, $P_t$ is the first public value, and $Gen(PV_t) \rightarrow (R_t, P_t)$ is an fuzzy extractor that generates from $PV_t$ the key $R_t$ and the first public value $P_t$.

20. The apparatus of claim 19 wherein the monitoring device is configured to decrypt the encrypted information using the key $R_t$.

21. The apparatus of claim 18 wherein the monitoring device is configured to include a physiological value sensor for measuring a dynamic physiological value V2, the dynamic physiological value V2 being the given physiological value measured by the monitoring device.

22. The apparatus of claim 18 wherein the given physiological value $PV_t$ is divided into two independent values, $PV1_t$ and $PV2_t$ with the monitoring device authenticating to the medical device using $PV1_t$ and the encrypted information received from the medical device being a non-redundant encryption of information of the information of the medical device using a key derived from $PV2_t$ generated by the medical device.

23. A method for use in an implanted medical device configured to communicate with an external monitoring device, the method comprising the steps of:
   measuring, in the medical device, one or more physiological values of a living organism in which the medical device is implanted; and
   controlling access to the medical device by the monitoring device based on the measured one or more physiological values;
   wherein access comprises an authorization to modify at least one function of the medical device;
   wherein the controlling step further comprises receiving a first public value from the monitoring device, generating a second public value and a key from a given physiological value measured by the medical device verifying the received first public value using the generated second public value, encrypting information of the medical device using the key responsive to the verification, and sending the second public value and the encrypted information to the monitoring device.

24. A non-transitory processor-readable storage medium having instruction code embodied therein which when executed by a processor implements the steps of the method of claim 23.

25. A method for use in an external monitoring device configured to communicate with an implanted medical device, the method comprising the steps of:
   measuring, in the monitoring device, one or more physiological values of a living organism in which the medical device is implanted; and
   obtaining access to the medical device based on the measured one or more physiological values;
   wherein access comprises an authorization to modify at least one function of the medical device; and
   wherein the obtaining step further comprises generating a first public value and a key from a given physiological value measured by the monitoring device, sending the first public value to the medical device, receiving a second public value and encrypted information from the medical device, verifying the received second public value using the generated first public value, and decrypting the encrypted information using the key responsive to the verification.

* * * * *